(12) United States Patent
Yu et al.

(10) Patent No.: US 11,672,634 B2
(45) Date of Patent: Jun. 13, 2023

(54) MEASURING SYSTEM AND METHOD FOR ANALYSIS OF SPACE FOR DENTAL IMPLANT RESTORATION

(71) Applicant: Sichuan University, Sichuan (CN)

(72) Inventors: Haiyang Yu, Sichuan (CN); Zhaozhao Chen, Sichuan (CN); Xi Chen, Sichuan (CN)

(73) Assignee: SICHUAN UNIVERSITY, Chengdu (CN)

( * ) Notice: Subject to any disclaimer, the term of this patent is extended or adjusted under 35 U.S.C. 154(b) by 1138 days.

(21) Appl. No.: 16/327,895

(22) PCT Filed: Mar. 27, 2018

(86) PCT No.: PCT/CN2018/080642
§ 371 (c)(1),
(2) Date: Feb. 25, 2019

(87) PCT Pub. No.: WO2019/085380
PCT Pub. Date: May 9, 2019

(65) Prior Publication Data
US 2021/0030520 A1    Feb. 4, 2021

(30) Foreign Application Priority Data

Nov. 2, 2017   (CN) .......................... 201711062017.X

(51) Int. Cl.
*A61C 19/05*     (2006.01)
*A61B 34/10*     (2016.01)
(Continued)

(52) U.S. Cl.
CPC ............ *A61C 19/05* (2013.01); *A61B 5/4547* (2013.01); *A61B 34/10* (2016.02); *A61C 19/04* (2013.01);
(Continued)

(58) Field of Classification Search
CPC .......... A61C 19/05; A61C 19/04; A61C 3/00; A61C 8/0089; A61C 8/009; A61B 5/4547; A61B 5/1072
(Continued)

(56) References Cited

U.S. PATENT DOCUMENTS 1,783,654 A * 12/1930 Kelsey ...................... A61C 3/00
                                                        30/68
1,800,714 A *  4/1931 Clap ....................... A61C 19/04
                                                       33/513
(Continued)

FOREIGN PATENT DOCUMENTS

CN       103690260          4/2014
CN       103690260 A    *  4/2014
(Continued)

OTHER PUBLICATIONS

Neumeyer Stefan, DE 102011055723 A1_translated (Year: 2013).*
(Continued)

*Primary Examiner* — Heidi M Eide
*Assistant Examiner* — Holly T. To
(74) *Attorney, Agent, or Firm* — Hauptman Ham, LLP

(57) ABSTRACT

A measuring system for analysis of space for dental implant restoration comprises a first measuring assembly for measuring a mouth opening degree and a first gap of plural missing teeth, a second measuring assembly for measuring a second gap of a single missing tooth and an occlusal distance, and a third measuring assembly for measuring a transgingival depth, wherein each of the first measuring assembly, the second measuring assembly and the third measuring assembly comprises a connecting rod and a measuring head disposed at an upper end of the connecting rod. A measuring method for analysis of space for dental
(Continued)

implant restoration using the aforesaid measuring system for analyzing is further disclosed.

13 Claims, 4 Drawing Sheets

(51) Int. Cl.
    *A61B 5/00*     (2006.01)
    *A61C 19/04*     (2006.01)

(52) U.S. Cl.
    CPC ... *A61B 2034/105* (2016.02); *A61B 2034/108* (2016.02)

(58) Field of Classification Search
    USPC ...................... 606/96, 102; 433/68
    See application file for complete search history.

(56) References Cited

U.S. PATENT DOCUMENTS

| | | | | |
|---|---|---|---|---|
| D294,470 S | * | 3/1988 | Jordan | D10/64 |
| 4,959,014 A | * | 9/1990 | Sheridan | A61C 19/04 33/514 |
| 4,997,368 A | * | 3/1991 | Mayer | A61C 19/04 33/514 |
| 5,044,951 A | * | 9/1991 | Sheridan | A61C 19/04 33/514 |
| 5,361,506 A | * | 11/1994 | Beeuwkes, III | A61C 19/04 33/514 |
| 5,423,677 A | * | 6/1995 | Brattesani | A61C 19/043 433/29 |
| 6,241,519 B1 | * | 6/2001 | Sedelmayer | A61C 19/04 433/141 |
| 6,347,940 B1 | * | 2/2002 | Gordils Wallis | A61C 8/0089 33/513 |
| 6,413,086 B1 | * | 7/2002 | Womack | A61C 19/04 33/513 |
| D739,529 S | * | 9/2015 | Tajima | D24/176 |
| D782,044 S | * | 3/2017 | Massad | D24/152 |
| 9,993,321 B1 | * | 6/2018 | Saiz | A61C 19/04 |
| 2003/0044751 A1 | * | 3/2003 | Deslauriers | A61C 19/04 378/168 |
| 2005/0191596 A1 | * | 9/2005 | Gordils Wallis | A61C 1/084 33/513 |
| 2005/0266372 A1 | * | 12/2005 | Chu | A61C 19/043 33/513 |
| 2007/0031788 A1 | * | 2/2007 | Chao | A61C 3/00 433/144 |
| 2007/0243498 A1 | * | 10/2007 | Wallis | A61C 19/04 433/72 |
| 2008/0145811 A1 | * | 6/2008 | Diers | A61C 19/04 206/569 |
| 2008/0241784 A1 | * | 10/2008 | Chung | A61C 19/04 433/76 |
| 2009/0042165 A1 | * | 2/2009 | Garrison | A61C 3/00 433/164 |
| 2011/0151406 A1 | * | 6/2011 | Solano | A61C 19/05 433/162 |
| 2015/0024339 A1 | * | 1/2015 | Calderon | A61C 19/04 433/72 |
| 2017/0296315 A1 | * | 10/2017 | Bakeman | A61C 19/04 |
| 2019/0083207 A1 | * | 3/2019 | Wagner | A61C 13/0006 |
| 2019/0104983 A1 | * | 4/2019 | Hussein | G09B 19/24 |
| 2020/0093582 A1 | * | 3/2020 | Wagner | A61B 3/111 |

FOREIGN PATENT DOCUMENTS

| | | | | |
|---|---|---|---|---|
| CN | 203763286 | | 8/2014 | |
| CN | 206463069 | | 9/2017 | |
| CN | 206463069 U | * | 9/2017 | ............ A61C 19/04 |
| CN | 107647929 | | 2/2018 | |
| CN | 109363788 A | * | 2/2019 | ............ A61C 19/04 |
| CN | 109431640 A | * | 3/2019 | ............ A61C 19/04 |
| CN | 110507444 A | * | 11/2019 | |
| CN | 111743654 A | * | 10/2020 | |
| CN | 112451150 A | * | 3/2021 | ............ A61C 19/04 |
| DE | 472074 C | * | 2/1929 | |
| DE | 20105192 U1 | * | 7/2001 | ............ A61C 19/05 |
| DE | 102007002622 A1 | * | 12/2007 | ............ A61C 19/04 |
| DE | 102011055723 A1 | * | 5/2013 | ............ A61C 19/04 |
| DE | 202019002752 U1 | * | 9/2019 | ............ A46B 17/02 |
| EP | 1530953 A1 | * | 5/2005 | ............ A61C 3/00 |
| FR | 3063215 B1 | * | 1/2020 | ............ A61C 19/04 |
| GB | 2185819 A | * | 7/1987 | ............ A61C 19/04 |
| GB | 2439926 A | * | 1/2008 | ............ A61C 19/04 |
| KR | 100860762 B1 | * | 9/2008 | ............ A61C 19/04 |
| KR | 20080082813 A | * | 9/2008 | ............ A61C 19/04 |
| KR | 20130034315 A | * | 4/2013 | ............ A61C 19/05 |
| KR | 101501954 B1 | * | 3/2015 | ............ A61C 3/00 |
| WO | WO-2007021099 A1 | * | 2/2007 | ............ A61C 1/084 |

OTHER PUBLICATIONS

Li C, "CN 112451150 Abstract Translate" (Year: 2021).*
Gao S, "CN 111743654 Abstract Translate" (Year: 2020).*
"Bertrand F, FR 3063215 Abstract Translate" (Year: 2020).*
Ding H, "CN 110507444 Abstract Translate" (Year: 2019).*
Breitschmid U, "DE 202019002752 Abstract Translate" (Year: 2019).*
Cheng C, "CN 109431640 Abstract Translate" (Year: 2019).*
Wang M, "CN 109363788 Abstract transalte" (Year: 2019).*
Chen Z, "CN 206463069 Abstract Translate" (Year: 2017).*
Cho Sang Choon, "KR 101501954 Abstract Translate" (Year: 2015).*
Hong Z, "CN 103690260 Abstract Translate" (Year: 2014).*
Neumeyer S, "DE 102011055723 Abstract translate" (Year: 2013).*
Kim Byung Ock, "KR20130034315A Abstract translate" (Year: 2013).*
Im Doo Man, "KR 20080082813 Abstract translated" (Year: 2008).*
Yoon In Han, "KR 100860762 Abstract Translated" (Year: 2008).*
Zipplies R, "DE 102007002622 Abstract Translated" (Year: 2007).*
Chung Y, "WO 2007021099 Abstract translated" (Year: 2007).*
James P M, "EP 1530953 Abstract translated" (Year: 2005).*
Hans Geys, "DE472074C_translated" (Year: 1929).*
International search report dated Jul. 24, 2018 from corresponding application No. PCT/CN2018/080642.

* cited by examiner

MEASURING SYSTEM AND METHOD FOR ANALYSIS OF SPACE FOR DENTAL IMPLANT RESTORATION

RELATED APPLICATIONS

The present application is a National Phase of International Application Number PCT/CN2018/080642, filed Mar. 27, 2018. and claims the priority of China Application No. 201711062017.X, filed Nov. 2, 2017.

FIELD OF THE INVENTION

The present invention relates to the technical field of analysis of space for dental implant restoration, and more particularly to a measuring system and method for analysis of space for dental implant restoration.

BACKGROUND OF THE INVENTION

At present, most clinicians adopt the model analysis and visual method for intraoral analysis, intraoral analysis highly dependent on the clinician's experience, prone to errors due to the effect of factors such as the inspection angle and sight line, and ignoring the examination of the mouth opening degree of patients (vertical distance between the upper and lower edges of central incisor at the maximum mouth opening) and occlusal distance (vertical distance between the upper surface of the implant and the jaw teeth when the upper and lower dentitions are in the widest contact), thereby resulting in problems such as difficulties in later restoration. Model analysis firstly prepares a denture model by making a female die of denture and pouring gypsum into the female die, and then measures the region to be repaired of the model. Since the region to be repaired of the denture model is in an irregular shape, the operation difficulty of measuring with a ruler is large, the operation process is complicated, and the measurement accuracy is poor, which is often necessary to rely on experience to perform secondary treatment on the data after the measurement.

To sum up, current intraoral and model analysis of space relies on clinical experience, and lacks of accurate and efficient measuring means as well as clear measuring methods and standards.

BRIEF SUMMARY OF THE INVENTION

The present invention aims to provide a measuring system for analysis of space for dental implant restoration. The measuring assemblies used in the measuring system have simple structures, are easy to use and provide accurate data in measuring, and are able to measure the specific spatial features of the region to be repaired precisely and quickly, which provides a basis for the design of key parameters such as size and implant position of the implant, or the shape and structure of the upper prosthesis, solving the problem that current intraoral and model analysis of space relies on clinical experience and lacks of accurate and efficient measuring means. The present invention also provides a measuring method for analysis of space for dental implant restoration.

The present invention is realized by the following technical scheme:

A measuring system for analysis of space for dental implant restoration comprises: a first measuring assembly for measuring a mouth opening degree and a first gap of plural missing teeth, a second measuring assembly for measuring a second gap of a single missing tooth and an occlusal distance, and a third measuring assembly for measuring a transgingival depth, wherein each of the first measuring assembly, the second measuring assembly and the third measuring assembly comprises a connecting rod and a measuring head disposed at an upper end of the connecting rod.

As a further improvement of the present invention, the measuring head of the first measuring assembly is T-shaped, and comprises a first square ruler and a second square ruler, a length of the first square ruler is greater than a length of the second square ruler, a lower end of the first square ruler is connected to the upper end of the connecting rod, and an upper end of the first square ruler is connected to a lower end of the second square ruler. The first square ruler and the second square ruler are perpendicular to the connecting rod in the lengthwise direction, and a front surface of an upper end of the second square ruler is provided with a scale along the lengthwise direction. The first measuring assembly in the scheme can be used for conventional implant surgery and digital guide plate implant surgery, the length of the two square rulers is preset according to the requirements of the two types of surgeries, so as to facilitate direct comparative measurement. When the patient open the mouth at maximal mouth opening, the measuring head is erected in the region to be repaired of the patient, the first square ruler and the second square ruler are vertically placed, and the lower end of the second square ruler is vertically contacted with the region to be repaired. The upper end of the second square ruler not blocked by the opposite jaw teeth means the mouth opening height is greater than the length of the second square ruler, so that the operation space for implant surgery of the patient meets the requirements for conventional implant surgery, otherwise the operation space for implant surgery is insufficient and the patient involved is not suitable for conventional implant surgery. Similarly, the lower end of the first square ruler is vertically contacted with the region to be repaired of the patient. The other end of the first square ruler not blocked by the opposite jaw teeth means the mouth opening height is greater than the length of the first square ruler, so that the operation space for implant surgery of the patient meets the requirements for digital guide plate implant surgery. Otherwise, the patient involved is not suitable for digital guide plate implant surgery. The maximum mouth opening degree of the patient is directly measured by the first measuring ruler, so as to simply and accurately judge whether the operation space for the surgery is sufficient, and avoid the consequences such as obstruction of surgical instruments and inability to perform operation caused by visual misjudgment. The first measuring assembly in the scheme can also be used for determining the number and implant position of implants for plural continuous missing teeth. When in use, the operator holds the first measuring assembly with the scale side facing upward, leans the side edge of the second square ruler against the adjacent side of the natural tooth near the first gap, and measures the central position of the future implant by using the scale on the front surface of the second square ruler, which can measure the first gap of plural missing teeth very conveniently, helping the operator select the position and type of the implant. In addition, the first measuring assembly can be both applied to the measurement of the mouth opening degree of the conventional implant surgery and the digital guide plate implant surgery, and the determination of the number and position of the implants for plural continuous missing teeth, achieving multiple purposes with one ruler, which avoids use of a plurality of tools, not only convenient for carrying and storage, but also effective in saving resources and costs.

As another further improvement of the present invention, the measuring head of the second measuring assembly comprises a first measuring ruler and a second measuring ruler, a lower end of the second measuring ruler is connected to the upper end of the connecting rod, the first measuring ruler and the second measuring ruler are perpendicular to each other, and one end of the first measuring ruler is connected to a side of the connecting rod.

Further, the second measuring ruler comprises a first measuring part, a second measuring part and a third measuring part which are sequentially connected from bottom to top, wherein the first measuring part, the second measuring part and the third measuring part are rectangular plates and widths thereof are reduced sequentially reduced, and a lower end of the first measuring part is connected to the upper end of the connecting rod. The first measuring part, the second measuring part and the third measuring part have preferably the same height in the vertical direction, and their widths are preset according to the width of the permanent lower anterior teeth and the accessional teeth. The inclined direction of the second measuring ruler is in line with the direction of the upper end of the connecting rod. The second measuring ruler can be used to measure the second gap of the single missing tooth. When in measuring, the distance between the most salient points on the adjacent surfaces near the second gap of two adjacent teeth in the region to be repaired is comparatively measured by using the second measuring ruler, judging whether the implant restoration can be conducted and selecting an appropriate implant by comparatively measuring the measuring part able to pass the second gap of the single missing tooth, allowing analyzing the second gap of the single missing tooth easily and directly, and eliminating the errors caused by visual inspection.

Further, the first measuring ruler comprises a sixth measuring part, a fourth measuring part and a fifth measuring part connected sequentially, wherein the fifth measuring part is disposed away from the connecting rod, and an end of the sixth measuring part away from the fourth measuring part is connected to a side of the upper end of the connecting rod.

Preferably, both the fifth measuring part and the fourth measuring part are rectangular plates, and a width of the fifth measuring part is less than a width of the fourth measuring part. The first measuring ruler in this scheme can be used to check the occlusal distance, and the dimensions of the fifth measuring part, the fourth measuring part and the sixth measuring part are preset according to the requirements of the intermaxillary distance. When measuring, the patient is requested to occlude to maintain the widest and closest contact between the upper and lower teeth, the operator holds the second measuring assembly to conduct comparative measurement. If the fourth measuring part can pass the occlusion gap, the intermaxillary distance is demonstrated to be large enough, thus the upper prosthesis could be fixed by binders or screws. If the fourth measuring part cannot pass and the fifth measuring part can pass, the intermaxillary distance is demonstrated to be medium, screw retention is preferred. If the fifth measuring part cannot pass, the intermaxillary distance and the restoration space are demonstrated to be too small to accommodate the abutment and the prosthesis, which is not suitable for the implant restoration. Occlusal distance checking can be performed simply and directly by using the first measuring ruler in this scheme to directly compare whether the first measuring ruler can pass through the occlusion gap in the region to be repaired, effectively solving the problem that the upper restoration cannot be completed due to insufficient occlusal distance, and providing accurate and reliable basis for selecting the retention method of the abutment (screw retention or binder retention).

As another further improvement of the present invention, the measuring head of the third measuring assembly comprises a ruler body, a lower end of the ruler body is connected to the upper end of the connecting rod, a lengthwise direction of the ruler body is the same as an orientation of the connecting rod, and a scale is provided on the ruler body along the lengthwise direction of the ruler body. The third measuring assembly in this scheme can be used for making model analysis or measuring the transgingival depth in the patient's mouth when analyzing space for dental implant restoration. After the final model of the patient is prepared, the operator keeps the third measuring assembly with a tip of the ruler body close to the upper edge of the implant and measures the transgingival depth with the scale. The transgingival depth of the abutment is obtained according to the depth of the gingiva inserted with the tip i.e. the ruler body. Meanwhile, the area 3-4 mm (ideal depth) from the scale tip is further marked as red, which allows visually judging the transgingival depth and whether a customized personalized abutment should be fabricated by the color without identifying a specific scale, further shortening the operation time.

As another further improvement of the present invention, the connecting rod comprises an upper connecting rod, a middle connecting rod and a lower connecting rod which are sequentially connected from top to bottom, wherein, in the three-dimensional Cartesian coordinate system, when a lower end of the lower connecting rod is placed at the origin o and the lower connecting rod is placed at the positive half of the y axis, and the middle connecting rod inclines toward the negative half of the z axis, therefore an included angle A is formed between the middle connecting rod and the lower connecting rod on the y-z plane, a lower end of the upper connecting rod is connected to the lower connecting rod, and the upper end inclines toward the positive half of the z axis and forms an included angle B with the middle connecting rod on the Y-Z plane. Since the oral cavity is a cavity where the teeth locate in, the angle B formed between the middle and upper connecting rods on the y-z plane allows the measuring ruler to pass over the lip and reach the region to be repaired, when the measuring ruler is inserted into the oral cavity by holding the lower connecting rod. (when measuring, the lip is located in the concave part at an included angle B formed between the middle connecting rod and the upper connecting rod, not blocking the ruler body.) As an included angle A is formed between the middle connecting rod and the lower connecting rod on the y-z plane, the hand of the operator and the working end of the measuring ruler are not on the same horizontal plane but on a lower plane, avoiding the measuring region to be blocked by the tissues, such as hand, out of the region to be repaired, which is beneficial for accurately data acquiring and recording. Wherein, the included angle A and the included angle B can be 120°-135°.

Further, the middle connecting rod also inclines toward the positive or negative half of the x axis, so the middle connecting rod and the upper connecting rod form an included angle C on the x-y plane. The included angle C ranges from 120° to 180° and is not equal to 180°; that is, an included angle is formed between the upper connecting rod and the y axis, and the included angle is not more than 60°. For the corners of the mouth often block the measuring ruler when measuring the region to be repaired in the deep part of the mouth, in this technical scheme, the angle formed between the middle connecting rod and the upper connecting rod on the x-y plane enables the working end of the measuring ruler to stretch into the deep part of the mouth over the corners of the mouth, thus reducing the blocking of the corners of the mouth and facilitating accurate data acquisition and recording.

The present invention also provides a measuring method for analysis of space for dental implant restoration which uses the aforesaid measuring system for analysis of space for dental implant restoration to analyze, wherein the method comprises intraoral analysis and measurement steps and/or model analysis and measurement steps;

The intraoral measurement and analysis comprises the steps of measuring an operation space, measuring the second gap of the single missing tooth, determining number and position of implants for plural continuous missing teeth, and checking the occlusal distance;

The preoperative model analysis and measurement comprises the steps of measuring the second gap of the single missing tooth, determining number and position of implants for plural continuous missing teeth, checking the occlusal distance, and measuring the transgingival depth;

In the step of measuring the operation space, the first measuring assembly is used to measure a maximum mouth opening height of a patient;

In the steps of measuring the second gap of the single missing tooth, the second measuring assembly is used to measure a distance between salient points of the adjacent surfaces near the second gap sides of two adjacent teeth in a region to be repaired of the patient;

In the steps of determining number and position of implants for plural continuous missing teeth, the first measuring assembly is used to measure the size of the first gap and determine the position of the center of the implants;

In the steps of checking the occlusal distance, the second measuring assembly is used to measure the intermaxillary distance of the patient.

In the step of measuring the transgingival depth, the third measuring assembly is used to measure the transgingival depth Compared to the existing art, the present invention has advantages and beneficial effects as follows:

1. The maximum mouth opening degree of the patient is directly measured by the first measuring ruler in the present invention, so as to simply and accurately judge whether the operation space is sufficient for the surgery, and avoid the consequences such as obstruction of surgical instruments and inability to perform operation caused by visual misjudgment.

2. The occlusal distance checking can be performed simply and directly by using the first measuring ruler of the second measuring assembly in the present invention to directly compare whether the first measuring ruler can pass through the occlusion gap in the region to be repaired, effectively solving the problem that the upper restoration cannot be completed due to insufficient occlusal distance, and providing accurate and reliable basis for selecting the retention method of the abutment (screw retention or binder retention).

3. The second gap of the single missing tooth analysis is performed easily and directly by using the second measuring ruler of the second measuring assembly in the present invention to directly compare whether second measuring ruler can pass the second gap in the measuring region to be repaired. The first gap of plural missing teeth can be comparatively measured by using the scale of the end of the second square ruler of the first measuring assembly in the present invention, helping the operator select the implant position and type of the implant;

4. The transgingival depth of the abutment is obtained according to the depth of the gingiva inserted with the tip of the third measuring assembly by using the third measuring assembly in the present invention, moreover, the area 3-4 mm (ideal depth) from the scale tip is marked as red, which allows visually judging the transgingival depth and whether a customized personalized abutment should be fabricated by the color without identifying a specific scale, further shortening the operation time.

In a word, the present invention realizes intraoral and model analyses of a series spaces for dental implant restoration by using three assemblies with specific shapes and structures in a combined way and making direct comparison with specific parts thereof. The measuring system in the present invention is simpler and more accurate than visual inspection or ordinary ruler, and can effectively measure the spatial characteristics of the region to be repaired, thereby providing a basis for the design of parameters such as size and implant position of the implant as well as shape and structure of the upper prosthesis.

BRIEF DESCRIPTION OF THE DRAWINGS

The figures described herein are used to provide a further understanding of the embodiments of the present invention and constitute a part of the present invention but without limiting the embodiments of the present invention. In the figures.

DETAILED DESCRIPTION OF THE PREFERRED EMBODIMENTS

Figure 1:
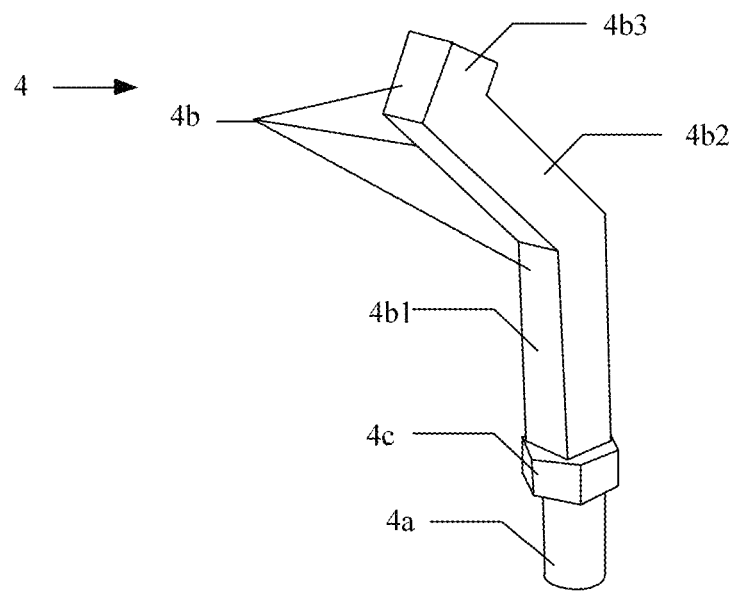
FIG. 1 is a schematic diagram of the connecting rod.

In order to make the purpose, technical scheme and advantages of the present invention understood more clearly, the present invention will be further described in detail in combination with drawings and preferred embodiments. The exemplary embodiments of the present invention and description thereof are used to explain the present invention, but not improperly limit thereto.

It is to be understood that the orientation or positional relationship indicated by the terms "front", "rear", "left", "right", "up", "down", "vertical", "horizontal", "high", "low", "inside", "outside" and the like in the description of the present invention are as indicated in the drawings, only for the convenience of describing the invention and simplifying the description, and not to indicate or imply that the device or element referred to must have a specific orientation, or be constructed and operated in a specific orientation, and therefore cannot be understood as limiting the scope of protection of the invention.

Example 1

A measuring system for analysis of space for dental implant restoration comprises a first measuring assembly for measuring a mouth opening degree and a first gap of plural missing teeth, a second measuring assembly for measuring a second gap of the single missing tooth and an occlusal distance, and a third measuring assembly for measuring a transgingival depth, wherein each of the first measuring assembly, the second measuring assembly and the third measuring assembly comprises a connecting rod and a measuring head disposed at an upper end of the connecting rod; that is, each measuring assembly has a connecting rod and a measuring head, namely, the measuring heads of the three measuring assemblies are different, and the connecting rods can be the same. In this example, the connecting rods of the three measuring assemblies have the same shape.

As shown in FIG. 1, the connecting rod 4 is a curved long rod and comprises a connecting rod body 4$b$, a connecting cylinder 4$a$ and a hexagonal body 4$c$, wherein the hexagonal body 4$c$ is a hexagonal prism with its upper end face, lower end face and cross section being regular hexagon, an upper end face of the hexagonal body 4$c$ is connected to a lower end of the connecting rod body 4$b$, a lower end face of the hexagonal body 4$c$ is connected to an upper end of the connecting cylinder 4$a$, and an axial direction of the connecting cylinder 4$a$ is vertical.

The connecting rod body 4$b$ comprises an upper connecting rod 4$b$3, a middle connecting rod 4$b$2 and a lower connecting rod 4$b$1 which are sequentially connected from top to bottom, the lower connecting rod 4$b$1 is vertically arranged, and both the upper connecting rod 4$b$3 and the middle connecting rod 4$b$2 are inclined to a certain extent. In the three-dimensional Cartesian coordinate system, if a lower end of the lower connecting rod 4$b$1 is placed at the origin o, and the lower connecting rod 4$b$1 is placed at the positive half of the y axis, then, the upper connecting rod 4$b$3 and the middle connecting rod 4$b$2 can be such positioned as to incline the middle connecting rod 4$b$2 toward the negative half of the z axis, therefore, an included angle A is formed between the middle connecting rod 4$b$2 and the lower connecting rod 4$b$1 on the y-z plane; a lower end of the upper connecting rod 4$b$3 is connected to middle connecting rod 4$b$2 an upper end of the upper connecting rod 4$b$3 is inclined toward the positive half of the z axis and forms an included angle B with the middle connecting rod 4$b$2. The included angles A and B both have an angle range of 120°-135°.

The middle connecting rod 4$b$2 is inclined toward the left side of the lower connecting rod 4$b$1 with the positive half axis direction of the x axis as the front and the negative half axis direction as the rear, the positive half axis direction of the y axis as the upper and the negative half axis directions as the lower, and the negative half axis direction of the z axis as the left and the positive half axis direction as the right, thus forming an included angle A with the middle connecting rod 4$b$2. The upper end of the upper connecting rod 4$b$3 is inclined toward the right with respect to its lower end and forms an included angle B with the middle connecting rod 4$b$2. The lower end of the lower connecting rod 4$b$1 is connected to the upper end face of the hexagonal body 4$c$. In this example, all of the cross sections of the upper connecting rod 4$b$3, the middle connecting rod 4$b$2 and the lower connecting rod 4$b$1 are square.

Figure 2:
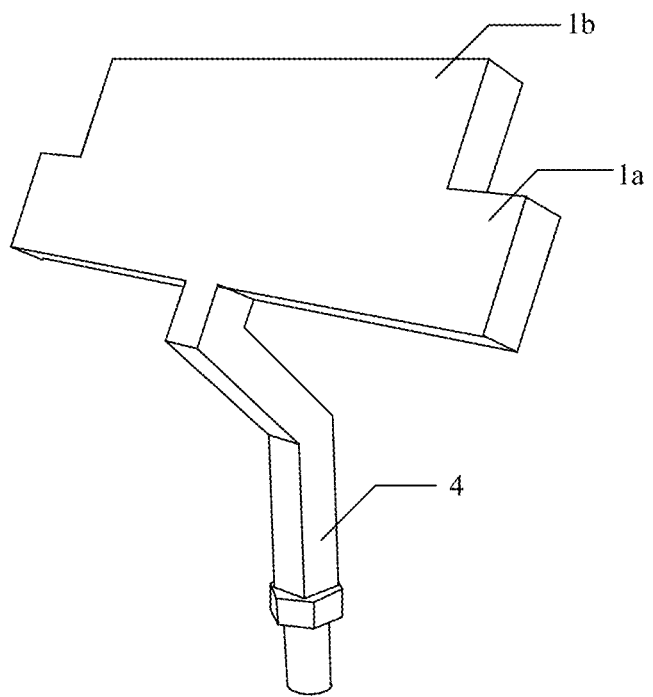
FIG. 2 is a schematic diagram of the first measuring assembly.

As shown in FIG. 2, the measuring head of the first measuring assembly is T-shaped, and comprises a first square ruler 1$a$ and a second square ruler 1$b$, a lower end of the first square ruler 1$a$ is connected to the upper end of the upper connecting rod 4$b$3 of the connecting rod 4, and an upper end of the first square ruler 1$a$ is connected to a lower end of the second square ruler 1$b$, forming a shape of "T". The lengthwise directions of the first square ruler 1$a$ and the second square ruler 1$b$ are perpendicular to an extension direction of the upper connecting rod 4$b$3.

A length L2 of the first square ruler 1$a$ is larger than a length L1 of the second square ruler 1$b$, and a thickness and a width of the first square ruler 1$a$ are the same as those of the second square ruler 1$b$. The front faces of the first square ruler 1$a$ and the second square ruler 1$b$ are on the same plane, and the back faces of the first square ruler 1$a$ and the second square ruler 1$b$ are also on the same plane. Thus, the first square ruler 1$a$ and the second square ruler 1$b$ are on the same plane as a whole. In fact, the first square ruler 1$a$ and the second square ruler 1$b$ can be integrally formed into a whole with uniform thickness.

Figure 3:
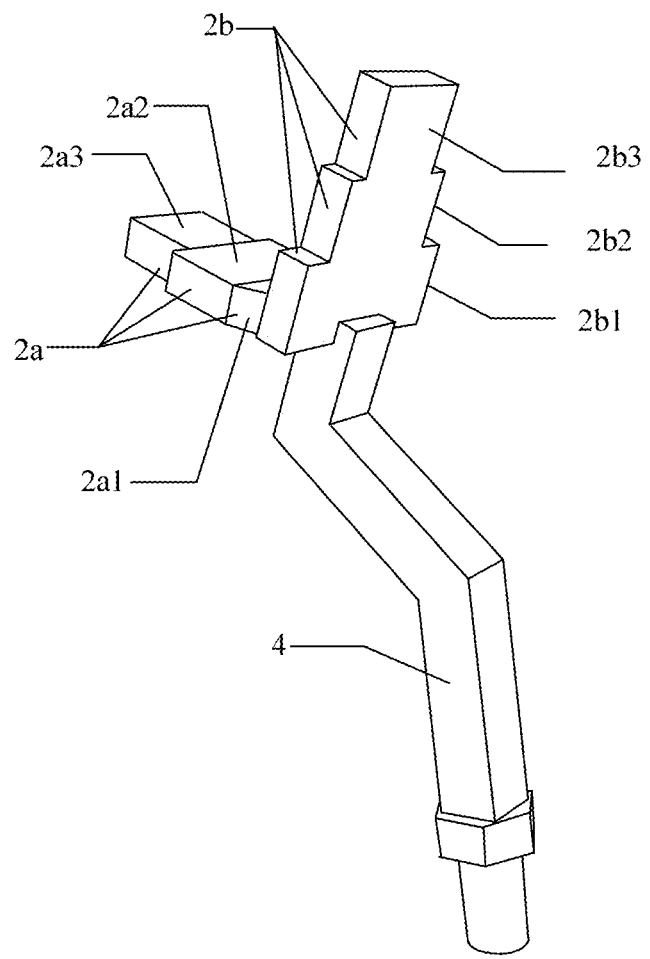
FIG. 3 is a schematic diagram of the second measuring assembly.

As shown in FIG. 3, the measuring head of the second measuring assembly comprises a first measuring ruler 2$a$ and a second measuring ruler 2$b$, the first measuring ruler 2$a$ and the second measuring ruler 2$b$ are perpendicular to each other. A lower end of the second measuring ruler 2$b$ is connected to the upper end of the upper connecting rod 4$b$3 of the connecting rod 4 of the second measuring assembly, and the installation direction of the second measuring ruler 2$b$ is the same as that of the upper connecting rod 4$b$3; that is, the included angle between the second measuring ruler 2$b$ and the middle connecting rod 4$b$2 is the same as the angle B. One end of the first measuring ruler 2$a$ is connected to a side of the upper connecting rod 4$b$3 away from the middle connecting rod 4$b$2, and extended toward the inclined direction of the middle connecting rod 4$b$2; that is, the first measuring ruler 2$a$ is located on the left side of the upper connecting rod 4$b$3, and the right side of the first measuring ruler 2$a$ is connected to the left side of the upper connecting rod 4$b$3.

The second measuring ruler 2$b$ comprises a first measuring part 2$b$1, a second measuring part 2$b$2 and a third measuring part 2$b$3 which are sequentially connected from bottom to top, wherein the first measuring part 2$b$1, the second measuring part 2$b$2 and the third measuring part 2$b$3 are rectangular plates and widths thereof are reduced sequentially reduced, and a lower end of the first measuring part 2$b$1 is connected to the upper end of the upper connecting rod 4$b$3.

The first measuring ruler 2$a$ comprises a sixth measuring part 2$a$1, a fourth measuring part 2$a$2, and a fifth measuring part 2$a$3 which are sequentially connected from right to left. The fifth measuring part 2$a$3 is disposed away from the upper connecting rod 4$b$3, and one end (i.e., right end) of the sixth measuring part 2$a$1 away from the fourth measuring part 2$a$2 is connected to the left side of the upper connecting rod 4$b$3.

Both the fifth measuring part 2$a$3 and the fourth measuring part 2$a$2 are rectangular plates and a width of the fifth measuring part 2$a$3 is less than a width of the fourth measuring part 2$a$2. The sixth measuring part 2$a$1 is an isosceles trapezoid plate with its long side connected to the fourth measuring part 2$a$2 and its short side connected to the left side of the upper connecting rod 4$b$3.

Figure 4:
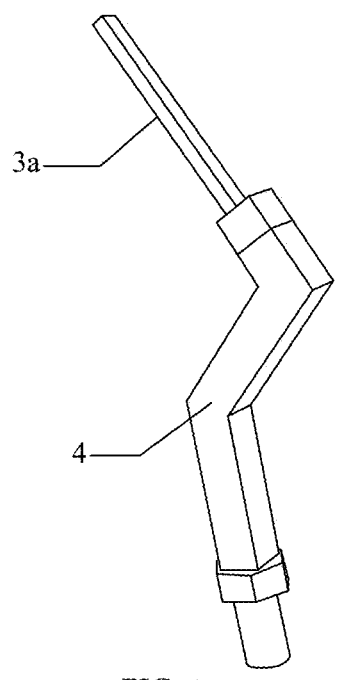
FIG. 4 is a schematic diagram of the third measuring assembly.

As shown in FIG. 4, the measuring head of the third measuring assembly comprises a ruler body 3a, a lower end of the ruler 3a is connected to the upper end of the upper connecting rod 4b3 of the connecting rod 4, the lengthwise direction of the ruler 3a is the same as the orientation of the upper connecting rod 4b3, and both the ruler 3a and the upper connecting rod 4b3 are inclined toward the negative half of the x axis. Meanwhile, the ruler 3a and the upper connecting rod 4b3 have the same orientation. In fact, the ruler 3a can be formed by extending the upper connecting rod 4b3 lengthwise, but the former is narrower than the latter. A scale is provided on the ruler 3a lengthwise.

Example 2

In this example, the connecting rod 4 is further improved on the basis of example 1:

When inclining toward the negative half of the z axis, the middle connecting rod 4b2 also inclines toward the negative half of the x axis, i.e. backward, thus, an included angle C is formed between the middle connecting rod 4b2 and the lower connecting rod 4b1 on the x-y plane. The included angle C ranges from 120° to 180° and not equal to 180°, that is, the angle formed between the middle connecting rod 4b2 and the positive half of the y axis is not more than 60°, in other words, the middle connecting rod 4b2 inclines backward with an inclined angle being within 60°.

Figure 7:
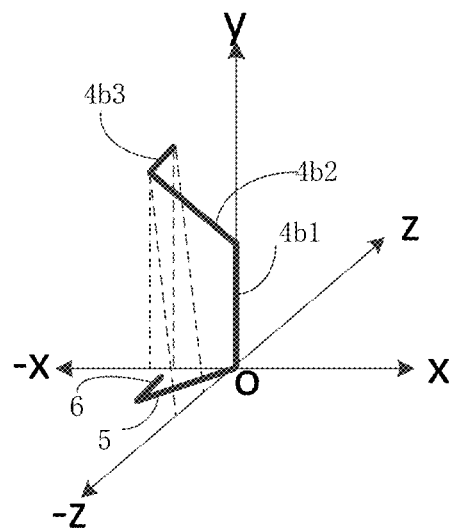
FIG. 7 is a schematic diagram of projections of the middle connecting rod and the upper connecting rod on the x-z plane according to example 2.

The projections of the upper connecting rod 4b3 and the middle connecting rod 4b2 on the x-y plane are as shown in FIG. 7, wherein 5 represents the projection of the middle connecting rod 4b2 on the x-z plane, and 6 represents the projection of the upper connecting rod 4b3 on the x-z plane.

In other examples, when the middle connecting rod 4b2 inclines toward the negative half of the z axis, it may also incline toward the positive half of the x axis, i.e., backward, at the same angle as in this example.

Example 3

This example is a further improvement of example 1, providing specific dimension for the measuring system for analysis of space for dental implant restoration in example 1.

(1) Connecting Rod

In this example, the connecting rods of the first measuring assembly, the second measuring assembly and the third measuring assembly are with identical structures and dimensions.

Figure 5:
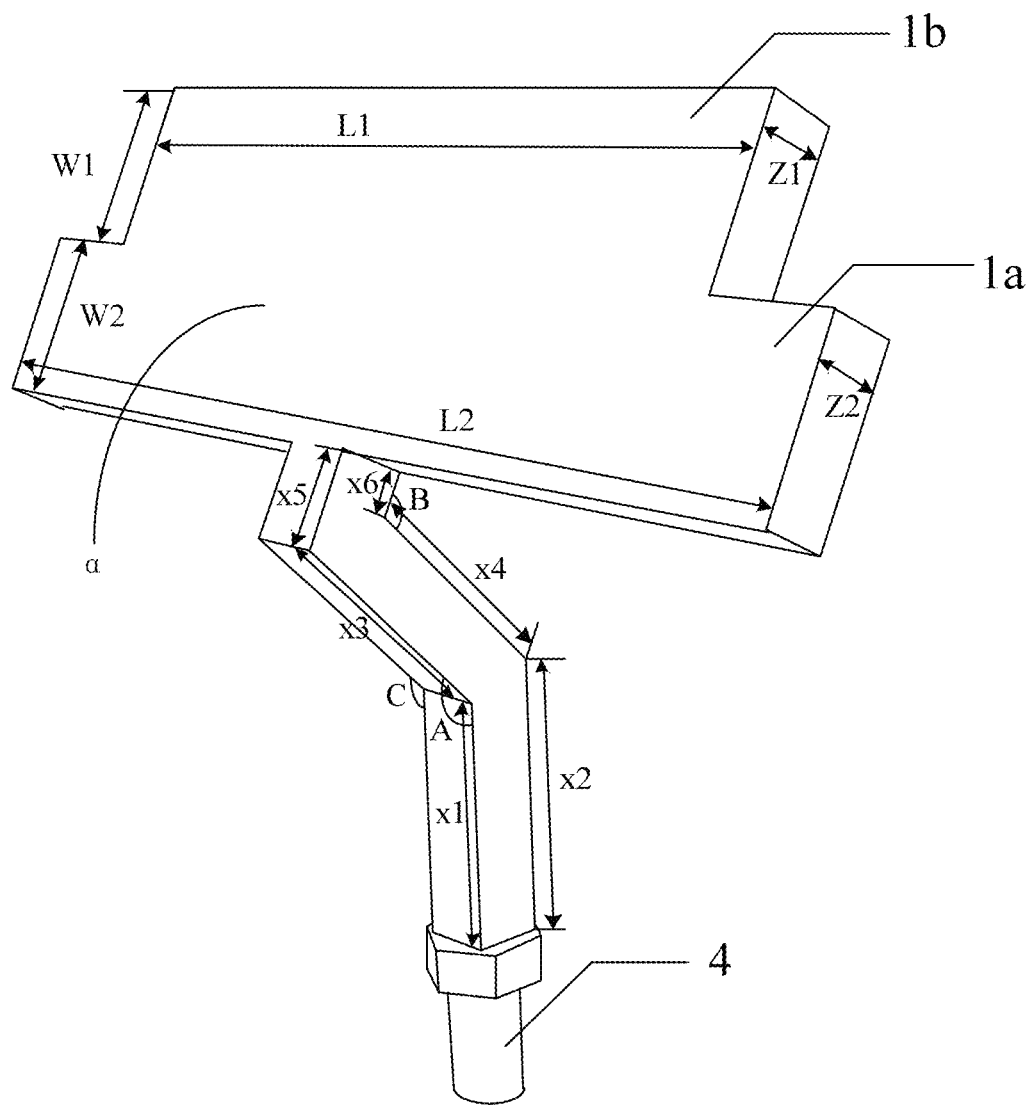
FIG. 5 is a schematic diagram of the first measuring assembly according to example 3.

In this example, the connecting rod is as shown in FIG. 5, the lower end of the connecting rod 4 is a connecting cylinder 4a with a length of 5 mm and a diameter of 3 mm, a hexagonal body 4c with a height of 2 mm and a side length of 2 mm is used as a connection of the connecting cylinder 4a and the connecting rod body 4b, the connecting rod body 4b is a curved long rod which has a square cross section with a 3 mm side length and has three sections which respectively are the upper connecting rod 4b3, the middle connecting rod 4b2 and the lower connecting rod 4b1, forming a shape of character "S".

The lower connecting rod 4b1 extends upward along a long axis direction of the connecting cylinder, that means, is vertically disposed, a left edge of the lower connecting rod 4b1 has a length of 11 mm and a right edge of lower connecting rod 4b1 has a length of 12 mm; the middle connecting rod 4b2 extends toward left, forming an include angle of 135° with the lower connecting rod 4b1, that means, the angle of the include angle A is 135° a left edge of the middle connecting rod 4b2 has a length of 11 mm and a right edge of middle connecting rod 4b2 has a length of 10 mm; the upper connecting rod 4b3 extends toward right, forming an include angle of 135° with the middle connecting rod 4b2, that means, the angle of the include angle A is 120°, a left edge of the upper connecting rod 4b3 has a length of 6 mm and a right edge of upper connecting rod 4b3 has a length of 4 mm;

(2) Measuring Head of the First Measuring Assembly

As shown in FIG. 5, the measuring head is a T-shaped ruler, the second square ruler 1b has a length L1 of 33 mm, a width W1 of 7 mm and a thickness Z1 of 3 mm, the scale is labeled in millimeters at the front surface the second square ruler 1b along the lengthwise direction, namely a direction of L1, the surface of the convex shaped ruler showed in FIG. 5 is the front surface, namely, surface a is the front surface, the first square ruler 1a has a length L2 of 43 mm, a width W2 of 7 mm and a thickness Z2 of 3 mm. When viewing from the side, the first square ruler 1a and the second square ruler 1b and the upper connection rod 4b3 of the connection rod 4 are in the same plane.

(3) Measuring Head of the Second Measuring Assembly

Figure 6:
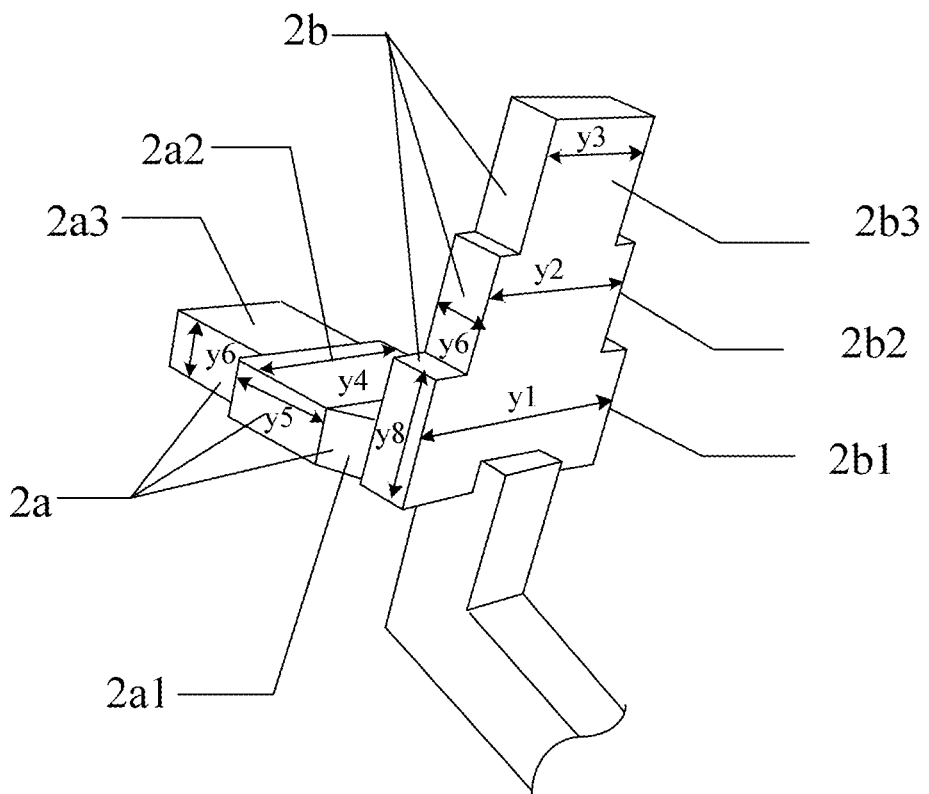
FIG. 6 is a schematic diagram of the second measuring assembly according to example 3.

As shown in FIG. 6, the measuring head of the first measuring assembly comprises two rulers with a shape similar to character "T" (the first measuring ruler 2a and a second measuring ruler 2b, both of which are connected with the upper connecting rod 4b3 of the connecting rod 4).

When viewing from the top, the sixth measuring part 2a1 of the first measuring ruler 2a has a shape of isosceles trapezoid with a length of the long side thereof 7 mm, a length of the short side 3 mm and a length of each oblique side 3.6 mm; the fifth measuring part 2a3 has a shape of rectangle with a length of the long side 5 mm and a length of the short side 4 mm; the fourth measuring part 2a2 has a shape of rectangle with a length of the long side y4 equal to 7 mm and a length of the short side y5 equal to 4 mm. In practice use, the sixth measuring part 2a1 is not limited to the shape and dimension in this example, can adopts trapezoid, rectangle or any other shapes, and can has other dimensions which do not affect measurement of the fourth measuring part 2a2.

When viewing from the left or the right in FIG. 3, the second measuring part 2b2 of the second measuring ruler 2b has a shape of rectangle with a length of the long side y2 equal to 7 mm and a length of the short side y1 equal to 4 mm; the first measuring part 2b1 has a shape of rectangle with a length of the long side y1 equal to 10 mm and a length of the short side y8 equal to 4 mm; the third measuring part 2b3 has a shape of rectangle with a length of the long side y3 equal to 5 mm and a length of the short side 4 mm.

The length of the long side of the fifth measuring part 2a3, the fourth measuring part 2a2, the first measuring part 2b1, a second measuring part 2b2 and the third measuring part 2b3 respectively are corresponding width of measuring parts, while the length of the short side respectively are the height of measuring parts.

The first measuring ruler and second measuring ruler 2b both have a thickness y6 equal to 2 mm.

In practical manufacturing, the sixth measuring part 2a1, the fourth measuring part 2a2 and the fifth measuring part 2a3 can be integrally formed into a whole with uniform thickness; and the first measuring part 2b1, the second measuring part 2b2 and the third measuring part 2b3 can be integrally formed into a whole with uniform thickness.

(4) Measuring Head of the Third Measuring Assembly

The ruler body 3a of an upper end of the measuring head of the third measuring assembly is a ruler has shape of character "1" which has a length of 15 mm, a width of 2 mm and a thickness of 1 mm when viewing from front.

In the measuring system for analysis of space for dental implant restoration according to this example, the first measuring assembly can be used for measuring the mouth opening degree and the first gap of plural missing teeth, the second measuring assembly is used for measuring the second gap of the single missing tooth and the occlusal distance, the third measuring assembly is used for measuring the transgingival depth. Functions, usage scenario and parameters of the three measure rulers are as shown in the table below.

In particular, the methods for using of and measuring with the three measuring assemblies and the method for analyzing and designing the dental implant restoration are as follows:

1) Preoperative Intraoral Analysis (1.1) Measuring the operation space for implant surgery Conventional implant surgery: The operator holds the first measuring assembly with the scale side facing forward, and instructs the patient to open his mouth to the maximum, then, erects the first measuring assembly in the region to be repaired of the patient, so as to comparatively measure the maximum mouth opening degree. When the patient opens

TABLE 1

Comparison table of main spatial parameters of dental implant

| | | Missing tooth gap | | | |
|---|---|---|---|---|---|
| | Mouth opening degree | Second Gap of the single missing tooth | First Gap of plural missing teeth | Occlusal distance | Transgingival depth |
| Spatial parameters and design methods of dental implants | >33 mm: meet the operation space requirement of surgery | >10 mm: preferably large-diameter implant | $D = R + 2$ mm | >7mm: binder retention/ screw retention of upper structure | Within the red area: finished abutment |
| | | 7-10 mm: preferably standard-diameter implant | $D = R + 1.5$ mm | 5-7 mm: preferably screw retention of upper structure | |
| | >43 mm: meet the operation space requirement of the digital guide plate implant surgery | 5-7 mm: preferably small-diameter implant | $D_{12} = R_1 + R_2 + 3$ mm | <5 mm: not suitable for implant restoration | Beyond red area: customized abutment |
| | | <5 mm: not suitable for implant restoration | | | |
| Corresponding measuring ruler of diagnostic kit | First measuring assembly | Second measuring assembly | First measuring assembly | Second measuring assembly | Third measuring assembly |

The measuring method comprises intraoral analysis and measurement steps and/or model analysis and measurement steps when the aforementioned measuring system is used for measuring and analyzing the space for the dental implant restoration;

The intraoral measurement and analysis comprises the steps of measuring the operation space, measuring the second gap of the single missing tooth, determining the number and position of implants for plural continuous missing teeth, and checking the occlusal distance;

The preoperative model analysis and measurement comprises the steps of measuring the second gap of the single missing tooth, determining the number and position of implants for plural continuous missing teeth, checking the occlusal distance, and measuring the transgingival depth;

In the step of measuring the operation space, the first measuring assembly is used to measure the maximum mouth opening height of the patient;

In the steps of measuring the second gap of the single missing tooth, the second measuring assembly is used to measure the distance between salient points of the adjacent surfaces near the second gap side of two adjacent teeth in a region to be repaired of the patient;

In the steps of determining the number and position of implants for plural continuous missing teeth, the first measuring assembly is used to measure the size of the first gap and determine the position of the center of the implants;

In the steps of checking the occlusal distance, the second measuring assembly is used to measure the intermaxillary distance of the patient;

In the step of measuring the transgingival depth, the third measuring assembly is used to measure the transgingival depth.

his mouth to the maximum, one end of the second square ruler 1b of the first measuring assembly vertically contacts the region to be repaired of the patient, the other end of the second square ruler 1b not blocked by the jaw teeth means the mouth opening height is greater than 33 mm and the operation space of the patient's implant surgery meet the requirements for conventional implant surgery. Otherwise, the operation space for implant surgery is insufficient and the patient is not suitable for performing the conventional implant surgery.

Digital guide plate implant surgery: The operator holds the first measuring assembly with the scale side facing forward, and instructs the patient to open his mouth to the maximum, then, the operator erects the first measuring assembly in the region to be repaired of the patient, so as to comparatively measure the maximum mouth opening degree. When the patient opens his mouth to the maximum, one end of the second square ruler 1a of the first measuring assembly is vertically contacts the region to be repaired of the patient, the other end of the second square ruler 1a not blocked by the jaw teeth means the mouth opening height is greater than 43 mm and the operation space of the patient's implant surgery meet the requirements for digital guide plate implant surgery. Otherwise, the patient is not suitable for performing the digital guide plate implant surgery.

(1.2) Measuring the second gap of the single missing tooth: The second measuring ruler 2b of the second measuring assembly comprises three widths, i.e. 10 mm of the first measuring part 2b1 located in the lower part, 7 mm of the second measuring part 2b2 located in the middle, and 5 mm of the third measuring part 2b3 located in the upper part.

The operator holds the second measuring assembly, instructs the patient to open his mouth wide, and measures the distance between the most salient points on the adjacent surfaces near the second gap between the two adjacent teeth in the region to be repaired by using the second measuring ruler 2b. If the first measuring part 2b1 at the lower part can pass the second gap, the gap width of the missing teeth is demonstrated to be greater than or equal to the average width of the permanent molars 10 mm, and a large-diameter implant (>4.5 mm) can be preferably selected. If the first measuring part 2b1 at the lower part cannot pass and the second measuring part 2b2 in the middle can pass the second gap, the gap width of missing teeth is demonstrated to be equal to a width of the permanent premolar, wherein the permanent premolar has a width of 7 mm to 10 mm thus an implant with a standard diameter of 3.5 mm to 4.5 mm can be preferably selected. If the second measuring part 2b2 in the middle cannot pass and the third measuring part 2b3 at the upper part can pass the second gap, the gap width of missing teeth is demonstrated to be equal to a width of the permanent mandibular anterior teeth, wherein, the permanent mandibular anterior teeth has s width of 5 mm to 7 mm, thus an implant with a small diameter (being not more than 3.5 mm) is preferably selected. If the third measuring part 2b3 at the upper part cannot pass the second gap, the second gap is demonstrated to be too narrow (<5 mm), which is not suitable for the implant restoration.

(1.3) Determining the number and position of implants for plural continuous missing teeth: The operator holds the first measuring assembly with the scale side facing upward, leans the side edge of the second square ruler 1b against the adjacent surface of the natural tooth near the first gap, and measures the position of the center of the future implant based on the scale on the front of the second square ruler 1b. The reference data are as follows: the ideal distance between the center of implant and the adjacent surface of the natural tooth near the first gap is D, wherein D=R (implant radius)+2 mm; the minimum distance between the center of implant and the adjacent side of the natural tooth near the first gap is d, wherein d=R+1.5 mm; and the minimum distance between the centers of the two implants is $d_{12}$, wherein $d_{12}=R_1+R_{2+3}$ mm.

(1.4) Checking the occlusal distance: The first measuring ruler 2a of the second measuring assembly comprises two widths, respectively are 7 mm of the fourth measuring part 2a2 in the middle and 5 mm of the fifth measuring part 2a3 at the end. The operator holds the second measuring assembly and instructs the patient to occlude to maintain the widest and closest contact between the upper and lower teeth, then, conducts comparative measurement by using the first measuring ruler 2a. If the fourth measuring part 2a2 in the middle can pass the occlusion gap, the intermaxillary distance is demonstrated to be more than 7 mm, the upper prosthesis could be fixed by binders or screws. If the fourth measuring part 2a2 in the middle cannot pass and the fifth measuring part 2a3 at the end can pass, the intermaxillary distance is demonstrated to be more than 5 mm and less than 7 mm, the screw retention is preferred. If the fifth measuring part 2a3 at the end cannot pass, the intermaxillary distance is demonstrated to be less than 5 mm and the restoration space are too small to accommodate the abutment and the prosthesis, which is not suitable for the implant restoration.

2) Preoperative Model Analysis (2.1) Measuring the second gap of the single missing tooth: After the study model of the patient is established, measuring the distance between the most salient points on the adjacent surfaces near the second gap of two adjacent teeth in the region to be repaired in the model by using the second measuring ruler 2b. If the first measuring part 2b1 at the lower part can pass the second gap, the gap width of the missing teeth is demonstrated to be greater than or equal to the average width of the permanent molars 10 mm, a large-diameter implant (>4.5 mm) can be preferably selected. If the first measuring part 2b1 at the lower part cannot pass and the second measuring part 2b2 in the middle can pass the second gap, the gap width of missing teeth is demonstrated to be equal to the width of the permanent premolar, wherein the width of the permanent premolar has a range from 7 mm to 10 mm thus, the implant with a standard diameter of 3.5 mm to 4.5 mm can be preferably selected. If the second measuring part 2b2 in the middle cannot pass and the third measuring part 2b3 at the upper part can pass the second gap, the gap width of missing teeth is demonstrated to be equal to the width of the permanent mandibular anterior teeth, wherein the width of the permanent mandibular anterior teeth has range from 5 mm to 7 mm, thus, the implant with a standard diameter being not more than 3.5 mm is preferably selected. If the third measuring part 2b3 at the upper part cannot pass the second gap, the second gap is demonstrated to be too narrow (<5 mm), which is not suitable for the implant restoration.

(2.2) Determining the number and location of implants for plural continuous missing teeth: after the patient study model is established, repeat step (1.3) on the model.

(2.3) Checking the occlusal distance: after the patient study model is established, occluding the upper and lower jaw models to maintain the widest and closest contact between the upper and lower teeth, then conducting comparative measurement by using the first measuring ruler 2a and holding the second measuring assembly by the operator. If the fourth measuring part 2a2 in the middle can pass the gap, the intermaxillary distance is demonstrated to be more than 7 mm, the upper prosthesis could be fixed by binders or screws. If the fourth measuring part 2a2 in the middle cannot pass the gap and the fifth measuring part 2a3 at the end can pass the gap, the intermaxillary distance is demonstrated to be more than 5 mm and less than 7 mm, the screw retention is preferred. If the fifth measuring part 2a3 at the end cannot pass the gap, the intermaxillary distance is demonstrated to be less than 5 mm, the restoration space are demonstrated to be too small to accommodate the abutment and the prosthesis, which is not suitable for the implant restoration.

3) Intraoral Analysis Before Upper Restoration (3.1) Checking the occlusal distance: repeating step (1.4) before taking the mold from the patient for implant restoration.

(3.2) Measuring the transgingival depth: before the model is taken from the patient for implant restoration, the operator holds the third measuring assembly for attaching the tip of the ruler body 3a to the upper edge of the implant with the ruler being perpendicular to the horizontal plane, and measures the transgingival depth with the scale. This value corresponds to the transgingival depth selected for the abutment. If the measured depth is within the red area, the finished abutment can be used. If the measured depth is beyond the red area, a customized abutment should be fabricated.

4) Model Analysis Before Upper Restoration (4.1) Measuring the transgingival depth: Fabricating the final model of the patient, attaching the tip of the ruler body 3a to the upper edge of the implant by holding the third measuring assembly by the operator, and measuring the transgingival depth with the scale. This value corresponds to the transgingival depth selected for the abutment. If the measured depth is within the red area, the finished abutment can be used. If the measured depth is beyond the red area, a customized abutment should be fabricated.

In this example:

The maximum mouth opening degree of the patient is directly measured by the first measuring ruler, so as to simply and accurately judge whether the operation space is sufficient for the surgery, and avoid the consequences such as obstruction of surgical instruments and inability to perform operation caused by visual misjudgment.

The occlusal distance checking can be performed simply and directly by using the first measuring ruler 2a of the second measuring assembly to directly compare whether the first measuring ruler can pass through the occlusion gap in the region to be repaired, effectively solving the problem that the upper restoration cannot be completed due to insufficient occlusal distance, and providing accurate and reliable basis for selecting the retention method of the abutment (screw retention or binder retention).

The second gap of the single missing tooth analysis is performed easily and directly by using the second measuring ruler 2b of the second measuring assembly in the present invention to directly compare whether second measuring ruler 2b can pass the first gap in the measuring region to be repaired. The first gap of plural missing teeth can be comparatively measured by using the scale of the end of the second square ruler 1b of the first measuring assembly in the present invention, helping the operator select the implant position and type of the implant.

The transgingival depth of the abutment is obtained according to the depth of the gingiva inserted with the tip of the third measuring assembly by using the third measuring assembly, moreover, the area 3-4 mm (ideal depth) from the scale tip is marked as red, which allows visually judging the transgingival depth and whether a customized personalized abutment should be fabricated by the color without identifying a specific scale, further shortening the operation time.

In a word, the measuring system of the present invention realizes intraoral and model analyses of a series of spaces for dental implant restoration by inventing assemblies with specific shapes and structures, using the assemblies in a combined way and making direct comparison with specific parts thereof. The measuring system is simpler and more accurate than visual inspection or ordinary ruler, and can effectively measure the spatial characteristics of the region to be repaired, thereby providing a basis for the design of parameters such as size and implant position of the implant as well as shape and structure of the upper prosthesis. In addition, this example also gives comprehensive and detailed spatial analysis and surgical design methods before surgery and restoration, which provides a scientific and reliable surgical plan for clinicians lacking of clinical experience and helps improve the success rate of dental implantation.

The aforementioned embodiments and examples further illustrate the purposes, technical solutions and beneficial effects of the present invention in detail. It is to be understood that the foregoing is only the embodiments of the present invention, and is not intended to limit the scope of the present invention. Any modifications, equivalent substitutes, improvements and the like made within the spirit and principle of the present invention should all be included in the scope of the present invention.

What is claimed is:

1. A measuring system for analysis of space for dental implant restoration, comprising: a first measuring assembly for measuring a mouth opening degree and a first gap of plural missing teeth, a second measuring assembly for measuring a second gap of a single missing tooth and an occlusal distance, and a third measuring assembly for measuring a transgingival depth, wherein each of the first measuring assembly, the second measuring assembly and the third measuring assembly comprises a connecting rod and a measuring head disposed at an upper end of the connecting rod, the measuring head of the second measuring assembly comprises a first measuring ruler and a second measuring ruler, a lower end of the second measuring ruler is connected to the upper end of the connecting rod, the first measuring ruler and the second measuring ruler are perpendicular to each other, and one end of the first measuring ruler is connected to a side of the connecting rod of the second measuring assembly;

the connecting rods of the first measuring assembly, the second measuring assembly and the third measuring assembly each comprise an upper connecting rod, a middle connecting rod and a lower connecting rod which are sequentially connected from top to bottom, wherein, in the three-dimensional Cartesian coordinate system, when a lower end of the lower connecting rod is placed at the origin o, and the lower connecting rod is placed at the positive half of the y axis, the middle connecting rod inclines toward the negative half of the z axis, therefore, an included angle A is formed between the middle connecting rod and the lower connecting rod on the y-z plane, a lower end of the upper connecting rod is connected to the middle connecting rod and an upper end of the upper connecting rod inclines toward the positive half of the z axis and forms an included angle B with the middle connecting rod.

2. The measuring system for analysis of space for dental implant restoration according to claim 1, wherein, the measuring head of the first measuring assembly is T-shaped, and comprises a first square ruler and a second square ruler, a length of the first square ruler is greater than a length of the second square ruler, a lower end of the first square ruler is connected to the upper end of the connecting rod, and an upper end of the first square ruler is connected to a lower end of the second square ruler.

3. The measuring system for analysis of space for dental implant restoration according to claim 2, wherein, the middle connecting rod also inclines toward the positive or negative half of the x axis, therefore, the middle connecting rod and the upper connecting rod form an included angle C on the x-y plane, the included angle C is greater than or equal to 120° and less than 180°.

4. The measuring system for analysis of space for dental implant restoration according to claim 1, wherein, the measuring head of the third measuring assembly comprises a ruler body, a lower end of the ruler body is connected to the upper end of the connecting rod of the third measuring assembly, a lengthwise direction of the ruler body is the same as an orientation of the connecting rod of the third measuring assembly, and a scale is provided on the ruler body along the lengthwise direction of the ruler body.

5. The measuring system for analysis of space for dental implant restoration according to claim 1, wherein, the middle connecting rod also inclines toward the positive or negative half of the x axis, therefore, the middle connecting rod and the upper connecting rod form an included angle C on the x-y plane, the included angle C is greater than or equal to 120° and less than 180°.

6. A measuring system for analysis of space for dental implant restoration, comprising: a first measuring assembly for measuring a mouth opening degree and a first gap of plural missing teeth, a second measuring assembly for measuring a second gap of a single missing tooth and an occlusal distance, and a third measuring assembly for measuring a transgingival depth, wherein
  each of the first measuring assembly, the second measuring assembly and the third measuring assembly comprises a connecting rod and a measuring head disposed at an upper end of the connecting rod,
  the measuring head of the second measuring assembly comprises a first measuring ruler and a second measuring ruler, a lower end of the second measuring ruler is connected to the upper end of the connecting rod, the first measuring ruler and the second measuring ruler are perpendicular to each other, and one end of the first measuring ruler is connected to a side of the connecting rod,
  the second measuring ruler comprises a first measuring part, a second measuring part and a third measuring part which are sequentially connected from bottom to top, wherein the first measuring part, the second measuring part and the third measuring part are rectangular plates and widths thereof are reduced sequentially reduced, and a lower end of the first measuring part is connected to the upper end of the connecting rod.

7. The measuring system for analysis of space for dental implant restoration according to claim 6, wherein, the first measuring ruler comprises a sixth measuring part, a fourth measuring part and a fifth measuring part connected sequentially, wherein the fifth measuring part is disposed away from the connecting rod, and an end of the sixth measuring part away from the fourth measuring part is connected to a side of the upper end of the connecting rod.

8. The measuring system for analysis of space for dental implant restoration according to claim 7, wherein, both the fifth measuring part and the fourth measuring part are rectangular plates, and a width of the fifth measuring part is less than a width of the fourth measuring part.

9. The measuring system for analysis of space for dental implant restoration according to claim 8, wherein, the connecting rods of the first measuring assembly, the second measuring assembly and the third measuring assembly each comprise an upper connecting rod, a middle connecting rod and a lower connecting rod which are sequentially connected from top to bottom, wherein, in the three-dimensional Cartesian coordinate system, when a lower end of the lower connecting rod is placed at the origin o, and the lower connecting rod is placed at the positive half of the y axis, the middle connecting rod inclines toward the negative half of the z axis, therefore, an included angle A is formed between the middle connecting rod and the lower connecting rod on the y-z plane, a lower end of the upper connecting rod is connected to the middle connecting rod and an upper end of the upper connecting rod inclines toward the positive half of the z axis and forms an included angle B with the middle connecting rod.

10. The measuring system for analysis of space for dental implant restoration according to claim 7, wherein, the connecting rods of the first measuring assembly, the second measuring assembly and the third measuring assembly each comprise an upper connecting rod, a middle connecting rod and a lower connecting rod which are sequentially connected from top to bottom, wherein, in the three-dimensional Cartesian coordinate system, when a lower end of the lower connecting rod is placed at the origin o, and the lower connecting rod is placed at the positive half of the y axis, the middle connecting rod inclines toward the negative half of the z axis, therefore, an included angle A is formed between the middle connecting rod and the lower connecting rod on the y-z plane, a lower end of the upper connecting rod is connected to the middle connecting rod and an upper end of the upper connecting rod inclines toward the positive half of the z axis and forms an included angle B with the middle connecting rod.

11. The measuring system for analysis of space for dental implant restoration according to claim 10, wherein, the middle connecting rod also inclines toward the positive or negative half of the x axis, therefore, the middle connecting rod and the upper connecting rod form an included angle C on the x-y plane, the included angle C is greater than or equal to 120° and less than 180°.

12. The measuring system for analysis of space for dental implant restoration according to claim 6, wherein, the connecting rods of the first measuring assembly, the second measuring assembly and the third measuring assembly each comprise an upper connecting rod, a middle connecting rod and a lower connecting rod which are sequentially connected from top to bottom, wherein, in the three-dimensional Cartesian coordinate system, when a lower end of the lower connecting rod is placed at the origin o, and the lower connecting rod is placed at the positive half of the y axis, the middle connecting rod inclines toward the negative half of the z axis, therefore, an included angle A is formed between the middle connecting rod and the lower connecting rod on the y-z plane, a lower end of the upper connecting rod is connected to the middle connecting rod and an upper end of the upper connecting rod inclines toward the positive half of the z axis and forms an included angle B with the middle connecting rod.

13. The measuring system for analysis of space for dental implant restoration according to claim 12, wherein, the middle connecting rod also inclines toward the positive or negative half of the x axis, therefore, the middle connecting rod and the upper connecting rod form an included angle C on the x-y plane, the included angle C is greater than or equal to 120° and less than 180°.

* * * * *